United States Patent [19]

Wörther et al.

[11] Patent Number: 5,099,021

[45] Date of Patent: Mar. 24, 1992

[54] PROCESS FOR THE PREPARATION OF PURE, UNSYMMETRICALLY DISUBSTITUTED UREAS

[75] Inventors: Rudolf H. Wörther; Horst Korntner; Egmont Auer; Kurt Thonhofer, all of Linz, Austria

[73] Assignee: Agrolinz Agrarchemikalien Gesellschaft M.B.H., Linz, Austria

[21] Appl. No.: 606,208

[22] Filed: Oct. 30, 1990

[30] Foreign Application Priority Data

Nov. 10, 1989 [AT] Austria .................. 2575/89

[51] Int. Cl.$^5$ ............................ C07D 401/00
[52] U.S. Cl. .................... 546/198; 546/209; 546/226; 548/163; 548/185; 548/196; 548/212; 548/213; 548/214; 548/217; 548/221; 548/222; 548/225; 548/228; 548/230; 548/233; 548/241; 548/244; 548/245; 548/246; 548/538; 564/48; 564/52; 564/53; 564/54
[58] Field of Search ......... 564/52, 53, 54, 48; 546/198, 209, 226; 548/163, 185, 196, 212, 213, 214, 217, 221, 222, 225, 228, 230, 233, 241, 244, 245, 246, 538

[56] References Cited

U.S. PATENT DOCUMENTS

| | | |
|---|---|---|
| 3,725,428 | 4/1973 | Janiak . |
| 4,212,981 | 7/1980 | Yukinaga et al. . |
| 4,310,692 | 6/1982 | Findeisen et al. ............... 564/61 |
| 4,380,641 | 4/1983 | Canada . |

FOREIGN PATENT DOCUMENTS

| | | |
|---|---|---|
| 0001251 | 4/1979 | European Pat. Off. . |
| 0002881 | 7/1979 | European Pat. Off. . |
| 0114456 | 8/1984 | European Pat. Off. . |
| 0296864 | 12/1988 | European Pat. Off. . |
| 1064051 | 2/1960 | Fed. Rep. of Germany . |
| 1259135 | 8/1968 | Fed. Rep. of Germany . |
| 1901501 | 8/1969 | Fed. Rep. of Germany . |
| 1288589 | 10/1969 | Fed. Rep. of Germany . |
| 1288607 | 10/1969 | Fed. Rep. of Germany . |
| 2436139 | 2/1975 | Fed. Rep. of Germany . |
| 2544367 | 4/1976 | Fed. Rep. of Germany . |
| 2818947 | 11/1978 | Fed. Rep. of Germany . |
| 2844962 | 4/1980 | Fed. Rep. of Germany . |
| 3151685 | 8/1982 | Fed. Rep. of Germany . |
| 3413755 | 10/1985 | Fed. Rep. of Germany . |
| 242803 | 2/1987 | German Democratic Rep. . |
| 81/02156 | 8/1981 | PCT Int'l Appl. . |

OTHER PUBLICATIONS

Chem. Abst., 100:156593q (1984) p. 534.
Chem. Abst., 90:54594y (1979) p. 579.
Chem. Abst., 82: 27104s (1975) p. 163.
Chem. Abst., 80: 108360h (1974) p. 404.
Chem. Abst., 77: 34357b (1972) p. 507.

*Primary Examiner*—Bruce Gray
*Attorney, Agent, or Firm*—Wenderoth, Lind & Ponack

[57] ABSTRACT

Process for the preparation of pure, unsymmetrically disubstituted ureas of the general formula

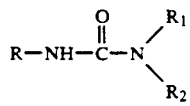

in which R denotes a phenyl radical which is unsubstituted, or monosubstituted or polysubstituted by halogen atoms or alkyl, alkoxy, aryloxy or trifluoromethyl groups, an oxazolyl, isoxazolyl, thiazolyl, isothiazolyl, benzoxazolyl or benzothiazolyl radical which is unsubstituted, or monosubstituted or polysubstituted by halogen atoms or alkyl, alkoxy or trifluoromethyl groups and R$_1$ and R$_2$ independently of one another denote a hydrogen atom or an alkyl group, where R$_1$ and R$_2$ are not simultaneously hydrogen or R$_1$ and R$_2$ together denote a butylene or pentylene group, by reaction of an N-alkyl- or N,N-dialkylurea with an unsubstituted or substituted arylamine or a heterocyclic amine in the presence of that amine which is already present in the starting material, the respective N-alkyl- or N,N-dialkylurea.

10 Claims, No Drawings

PROCESS FOR THE PREPARATION OF PURE, UNSYMMETRICALLY DISUBSTITUTED UREAS

The present invention relates to a process for the preparation of pure, unsymmetrically disubstituted ureas, starting from N-alkyl- or N,N-dialkylureas.

N-alkyl- or N,N-dialkylureas can be prepared, for example, by reaction of urea with N-alkyl- or N,N-dialkylamines according to U.S. Pat. No. 4,310,692. According to DE-A-1,064,051, such ureas should react with aryl- or cycloalkylamines to give unsymmetrically disubstituted ureas. As is already evident, however, from the comparison of the melting points given therein with the melting points known from the literature, only mixtures of different ureas and impure products are obtained according to DE-A-1,064,051.

It has now unexpectedly been found that pure, unsymmetrically disubstituted ureas can be prepared if N-alkyl- or N,N-dialkylureas are reacted with an unsubstituted or substituted arylamine or a heterocyclic amine in the presence of that amine which is already present in the starting material, the respective N-alkyl- or N,N-dialkylurea.

The invention therefore relates to a process for the preparation of pure, unsymmetrically disubstituted ureas of the general formula

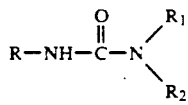

I in which R denotes a phenyl radical which is unsubstituted, or monosubstituted or polysubstituted by halogen atoms or alkyl, alkoxy, aryloxy or trifluoromethyl groups, an oxazolyl, isoxazolyl, thiazolyl, isothiazolyl, benzoxazolyl or benzothiazolyl radical which is unsubstituted, or monosubstituted or polysubstituted by halogen atoms or alkyl, alkoxy or trifluoromethyl groups and $R_1$ and $R_2$ independently of one another denote a hydrogen atom or an alkyl group, where $R_1$ and $R_2$ are not simultaneously hydrogen or $R_1$ and $R_2$ together denote a butylene or pentylene group, comprising reacting an N-alkyl- or N,N-dialkylurea of the general formula

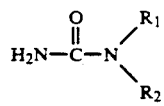

II in which $R_1$ and $R_2$ have the abovementioned meaning, in a diluent or not, with an amine of the general formula

                                       III in which R has the abovementioned meaning, in the presence of an excess of an amine of the general formula

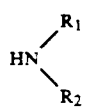

IV in which $R_1$ and $R_2$ in each case have the same meaning as in the N-alkyl- or N,N-dialkylurea employed of the general formula II and isolating the reaction product of the general formula I in a customary manner.

In the general formula I, R denotes a phenyl radical which is unsubstituted, or monosubstituted or polysubstituted by halogen atoms such as fluorine, chlorine or bromine, straight-chain, branched or cyclic alkyl groups having 1 to 6 C atoms, such as methyl, ethyl or propyl groups and their isomers, such as isopropyl, sec.butyl or tert. butyl groups or cyclopropyl, cyclopentyl or cyclohexyl groups, alkoxy groups having 1 to 5 C atoms, such as methoxy, ethoxy or propoxy groups, unsubstituted or substituted aryloxy groups such as phenoxy, p-chlorophenoxy or p-methoxyphenoxy groups or trifluoromethyl groups, among which mixed substituted phenyl radicals are also to be understood, or an oxazolyl, isoxazolyl, thiazolyl, isothiazolyl, benzoxazolyl or benzothiazolyl radical, which is unsubstituted, or monosubstituted or polysubstituted by halogen atoms, or alkyl, alkoxy or trifluoromethyl groups, the above-mentioned groups being suitable as halogen atoms and as alkyl and alkoxy groups. $R_1$ and $R_2$ independently of one another denote a hydrogen atom or a straight-chain, branched or cyclic alkyl group having 1 to 10 C atoms such as, for example, a methyl, ethyl, propyl, butyl or octyl group or one of their isomers such as, for example, an isopropyl, sec. butyl or tert. butyl group or a cyclopentyl, alkylcyclopentyl, cyclohexyl or alkylcyclohexyl group, where $R_1$ and $R_2$ are not simultaneously hydrogen or $R_1$ and $R_2$ together denote a butylene or pentylene group.

If R denotes a phenyl radical, compounds of the general formula I are preferred in which R denotes a phenyl radical which is unsubstituted, or monosubstituted or polysubstituted by halogen atoms, alkyl, alkoxy or aryloxy groups or trifluoromethyl groups and $R_1$ and $R_2$ independently of one another denote a hydrogen atom, a straight-chain or branched alkyl group having 1 to 6 C atoms or a cyclic alkyl group having 3 to 10 C atoms. Particularly preferred in this connection are compounds of the general formula I in which R denotes a phenyl radical which is unsubstituted, or monosubstituted or polysubstituted by halogen atoms, or alkyl, alkoxy, aryloxy or trifluoromethyl groups and $R_1$ and $R_2$ independently of one another denote a hydrogen atom or a straight-chain alkyl group having 1 to 4 C atoms.

If R denotes one of the abovementioned heterocyclic amines, compounds of the general formula I are preferred in which R denotes an isoxazolyl or benzothiazolyl radical which is unsubstituted or substituted as indicated above. Particularly preferred in this connection are compounds in which R denotes a benzothiazolyl radical which is unsubstituted or substituted as indicated above, very particularly preferably a benzothiazolyl radical which is unsubstituted or substituted by alkoxy groups.

Preferred unsymmetrically disubstituted ureas are those which are employed as herbicidal or fungicidal active compounds in plant protection. Examples of such compounds are known to the trade under the names fenuron, siduron, monuron, diuron, neburon, chlortoluron, metoxuron, isoproturon, chloroxuron, difenoxuron, fluometuron, benzthiazuron and isouron.

To carry out the process, an N-alkyl- or N,N-dialkylurea of the general formula II (urea II), which can be prepared, for example, by U.S. Pat. No. 4,310,692, is reacted with an amine of the general formula III (amine III), in the presence of an amine of the general formula IV (amine IV). In the amine IV, $R_1$ and $R_2$ in each case have the same meaning as in the urea II employed.

The reaction is carried out at temperatures from about 130° to 250° C. in the presence of a diluent or, alternatively, in the melt. Preferably, the reaction is carried out in a diluent. Under the reaction conditions, possible diluents are inert organic diluents. Examples of such diluents are, for example, amides such as dimethylformamide or dimethylacetamide, ketones, such as cyclohexanone, aliphatic and aromatic hydrocarbons, which are chlorinated or not, such as decalin, xylene or tetralin or chlorobenzenes, such as monochlorobenzene, dichlorobenzenes or trichlorobenzenes. Chlorobenzenes are preferred, and trichlorobenzenes are particularly preferred.

The urea II is initially introduced, if desired in a diluent, with an amine III. It can be initially introduced in an equimolar amount to the amine III or in an excess, but is preferably initially introduced in an excess. Particularly preferably, 0.5 to 0.7 mol of amine III is employed per mol of urea II. The reaction mixture is stirred and heated, the amine IV being added. The addition of the amine IV can be started at room temperature, but the amine IV is preferably only added at a temperature which is higher than room temperature.

Particularly preferably, the addition of the amine IV is started at temperatures from 60° to 120° C. If the reaction is carried out in the melt, the amine IV can also only be added if the reaction mixture is already liquid. The amine IV can be added in gaseous, liquid or solid form. Amines which are gaseous at room temperature can be introduced into the reaction mixture as such or dissolved in one of the abovementioned diluents. Amines which are not gaseous at room temperature can be converted into the gaseous state before addition by heating and added in gaseous form, but they can also be added as such or dissolved in one of the abovementioned diluents. Solid amines can be added, for example, with the aid of a screw conveyor. Liquid or dissolved amines are added dropwise or introduced via a nozzle, gaseous amines are passed in a customary manner. If the amine IV is dissolved before the addition, that diluent is preferably used in which the reaction is carried out. The amine IV is employed here in an excess relative to the urea II. Preferably, 2 to 15, particularly preferably 2 to 10, mol of the amine IV are added per mol of the urea II.

The amine IV is not added in one portion, it is continuously added in the course of the reaction. During the addition of the amine IV, the reaction mixture is heated to about 130° to 250° C., preferably to 160° to 225° C. In general, the reaction proceeds at normal pressure, although it can be carried out under pressure, it being possible to use pressures up to 20 bar.

The ammonia formed in the reaction is led off in a customary manner. When using a gaseous amine IV, a mixture of ammonia and excess amine IV is formed, which is led off and can be separated in a customary manner.

The amine IV separated off can be employed again in the reaction.

After the completion of the reaction, the reaction mixture is cooled. If the reaction was carried out in the melt, the reaction product of the general formula I crystallizes out in this case.

If the reaction was carried out in a diluent, the precipitate which may have deposited is filtered off or the diluent is removed by distillation. The crude product obtained in each case can be purified in a customary manner.

Preferably, the crude product is boiled in water for purification and the mixture is cooled. The precipitate is filtered off with suction and dried. In general, the purity of the product purified in this manner is excellent. For special purposes, however, a further purification, for example by recrystallization or chromatography, can additionally be added.

In a preferred embodiment, N,N-dimethylurea in trichlorobenzene is initially introduced with an amine III in which R denotes an unsubstituted or substituted phenyl radical, with stirring and the mixture is heated to 40° to 100° C. Hereupon, dimethylamine is continuously introduced, the reaction mixture being heated further to about 180° to 220° C. After completion of the reaction, the mixture is cooled to room temperature and the precipitate which may have deposited is filtered off or the diluent is removed by distillation. The crude product obtained in each case is freed from the diluent in a customary manner and boiled with water. The mixture is cooled, and the precipitate is filtered off with suction and dried.

In a particularly preferred embodiment, the urea II is prepared by reacting urea with an amine IV, for example according to U.S. Pat. No. 4,310,692, in the reaction vessel in which the reaction according to claim 1 is subsequently carried out, without the urea II being isolated.

It has proved to be particularly expedient to employ the mother liquors obtained when filtering off the reaction products from the diluent used again and again for a new reaction for the preparation of the same reaction products, since the yields increase greatly as a result, the purity of the reaction products unexpectedly remaining equally good.

With the aid of the process according to the invention, the products of the general formula I are obtained in excellent purity and good yields. The process thus represents an enrichment of the art.

EXAMPLE 1

N-(4-isopropylphenyl-N',N'-dimethylurea 3.35 g (0.038 mol) of N,N-dimethylurea and 3.38 g (0.025 mol) of 4-isopropylaniline were added with stirring into 20 ml of 1,2,4-trichlorobenzene. The reaction mixture was heated to 205° C., dimethylamine being introduced from 120° C. After 5.5 hours, 8.8 g (0.19 mol) of dimethylamine had been introduced and the reaction was complete.

The reaction mixture was cooled to room temperature, whereupon a precipitate deposited. The precipitate was filtered off, washed with 1,2,4-trichlorobenzene, dried and then boiled in 100 ml of water. The aqueous mixture was cooled, and the precipitate was filtered off with suction and dried. 4.0 g of N-(4-isopropylphenyl)-N',N'-dimethylurea, which corresponds to 78% of theory, having a melting point of 155° to 156° C. and a purity of 98.7% were obtained in this way.

EXAMPLE 1a

Using the same amount of 4-isopropylaniline and N,N-dimethylurea as in Example 1, but using the mother liquor obtained according to Example 1 instead of pure 1,2,4-trichlorobenzene as the diluent, 4.55 g of N-(4-isopropylphenyl)-N',N'-dimethylurea, i.e. 88% of theory, having a melting point of 155° to 157° C. and a purity of 97% were obtained in the same manner as in Example 1.

EXAMPLE 1b

The process was carried out as Example 1a, but using the mother liquor from Example 1a as the diluent.

Yield: 4.75 g, which corresponds to 92% of theory; Melting point: 155°-157° C.; Purity: 100%.

EXAMPLE 1c

The process was carried out as Example 1b, but using the mother liquor from Example 1b as the diluent.

Yield: 4.6 g, which corresponds to 89% of theory; Melting point: 155°-157° C.; Purity: 99.9%.

EXAMPLE 1d

The process was carried out as Example 1c, but using the mother liquor from Example 1c as the diluent.

Yield: 4.65 g, which corresponds to 90% of theory; Melting point: 155°-157° C.; Purity: 98.3%.

EXAMPLE 1e

The process was as Example 1d, but using the mother liquor from Example 1d as the diluent.

Yield: 4.6 g, which corresponds to 89% of theory; Melting point: 155°-157° C.; Purity: 99.2%.

EXAMPLE 2

N-(4-bromophenyl)-N',N'-dimethylurea 3.35 g (0.038 mol) of N,N-dimethylurea and 4.3 g (0.025 mol) of 4-bromoaniline were added with stirring into 28 ml of 1,2,4-trichlorobenzene, after which the mixture was slowly heated to 205° C. Dimethylamine was introduced from 50° C. After 5.5 hours, 11.6 g (0.25 mol) of dimethylamine had been introduced, and the reaction was complete. The reaction mixture was cooled to room temperature whereupon a precipitate deposited, which was filtered off, washed with 1,2,4-trichlorobenzene, dried at 100° C. in vacuo and then boiled in 100 ml of water. The aqueous mixture was cooled, and the precipitate was filtered off with suction and dried. 4.73 g of N-(4-bromophenyl)-N',N'-dimethylurea, i.e. 78% of theory, having a melting point of 168° to 170° C. were obtained in this way.

EXAMPLE 3

N-(4-chlorophenyl)-N',N'-dimethylurea

Using 3.19 g (0.025 mol) of 4-chloroaniline, 3.35 g (0.038 mol) of N,N-dimethylurea and 10.8 g (0.23 mol) of dimethylamine, 4.05 g of N-(4-chlorophenyl)-N',N'-dimethylurea, i.e. 82% of theory, having a melting point of 170° to 173° C. and a purity of 100% were obtained in the manner described in Example 2.

EXAMPLE 3a

N-(4-chlorophenyl)-N',N'-dimethylurea

In the manner described in Example 3 and using the same amounts of 4-chloroaniline and dimethylurea, but using the mother liquor obtained in Example 3 instead of pure 1,2,4-trichlorobenzene as the diluent and an amount of 12.8 g (0.28 mol) of dimethylamine, 4.45 g of N-(4-chlorophenyl)-N',N'-dimethylurea, i.e. 90% of theory, having a melting point of 170° to 173° C. and a purity of 99% were obtained.

EXAMPLE 4

N-(3-trifluoromethylphenyl)-N',N'-dimethylurea

Using 4.03 g (0.025 mol) of 3-trifluoromethylaniline, 3.35 g (0.038 mol) of N,N-dimethylurea and 13.1 g (0.28 mol) of dimethylamine, 4.35 g of N-(3-trifluoromethylphenyl)-N',N'-dimethylurea, i.e. 75% of theory, having a melting point of 160° to 161° C. and a purity of 99.2% were obtained in the manner described in Example 2.

EXAMPLE 4a

N-(3-trifluoromethylphenyl)-N',N'-dimethylurea

Using the amount of 3-trifluoromethylaniline and N,N-dimethylurea indicated in Example 4, but using the mother liquor from Example 4 instead of pure 1,2,4-trichlorobenzene as the diluent and using 11.4 g (0.25 mol) of dimethylamine, 4.8 g of N-(3-trichloromethylphenyl)-N',N'-dimethylurea, i.e. 83% of theory, having a melting point of 160° to 161° C. and a purity of 99.7% were obtained in the manner described in Example 2.

EXAMPLE 5

N-(3-chloro-4-methylphenyl)-N',N'-dimethylurea

Using 3.54 g (0.025 mol) of 3-chloro-4-methylaniline, 3.35 g (0.038 mol) of N,N-dimethylurea and 14.5 g (0.31 mol) of dimethylamine, 3.85 g of N-(3-chloro-4-methylphenyl)-N',N'-dimethylurea, i.e. 72% of theory, having a melting point of 142° to 147° C. and a purity of 99.3% were obtained in the manner described in Example 2.

EXAMPLE 6

N-(3,4-dichlorophenyl)-N',N'-dimethylurea

Using 4.05 g (0.025 mol) of 3,4-dichloroaniline, 3.35 g (0.038 mol) of N,N-dimethylurea and 11.0 g (0.24 mol) of dimethylamine, 4.7 g of N-(3,4-dichlorophenyl)-N',N'-dimethylurea, i.e. 81% of theory, having a melting point of 153° to 156° C. and a purity of 99.4% were obtained in the manner described in Example 2.

EXAMPLE 7

N-phenyl-N',N'-dimethylurea 3.35 g (0.038 mol) of N,N-dimethylurea and 2.33 g (0.025 mol) of aniline were added with stirring into 28 ml of 1,2,4-trichlorobenzene. The reaction mixture was slowly heated to 205° C., dimethylamine being passed in from 60° C. After 5.5 hours, 11.8 g (0.27 mol) of dimethylamine had been passed in and the reaction was complete. The reaction mixture was cooled to room temperature, whereupon a precipitate deposited. The precipitate was filtered off, washed with 1,2,4-trichlorobenzene, dried and then boiled in water. The aqueous mixture was cooled, and the precipitate was filtered off with suction and dried. 3.3 g of N-phenyl-N',N'-dimethylurea, i.e. 81% of theory, having a melting point of 130° to 133° C. were obtained in this way.

EXAMPLE 8

N-(4-methoxyphenyl)-N',N'-dimethylurea

Using 3.08 g (0.025 mol) of 4-methoxyaniline, 3.35 g (0.038 mol) of N,N-dimethylurea and 15.0 g (0.34 mol) of dimethylamine, 3.1 g of N-(4-methoxyphenyl)-N',N'-dimethylurea, i.e. 64% of theory, having a melting point of 126° to 130° C. were obtained in the manner described in Example 7.

EXAMPLE 9

N-(benzothiazol-2-yl)-N',N'-dimethylurea

Using 3.76 g (0.025 mol) of 2-aminobenzothiazole, 3.35 g (0.038 mol) of N,N-dimethylurea and 15.7 g (0.36 mol) of dimethylamine, the introduction time being 4 hours, 4.2 g of N-(benzothiazol-2-yl)-N',N'-dimethylurea, i.e. 76% of theory, having a melting point of 214° to 216° C. were obtained in the manner described in Example 7.

EXAMPLE 10

N-(6-ethyloxybenzothiazol-2-yl)-N',N'-dimethylurea

Using 4.86 g (0.025 mol) of 2-amino-6-ethoxybenzothiazole, 3.35 g (0.038 mol) of N,N-dimethylurea and 13.3 g (0.30 mol) of dimethylamine, 3.7 g of N-(6-ethoxybenzothiazol-2-yl)-N',N'-dimethylurea, i.e. 56% of theory, having a melting point of 183° to 186° C. were obtained in the manner described in Example 7.

EXAMPLE 11

N-(4-ethoxyphenyl)-N'-N'-diethylurea 3.43 g (0.025 mol) of 4-ethoxyaniline and 4.41 g (0.038 mol) of N,N-diethylurea in 25 ml of 1,2,4-trichlorobenzene were heated with stirring to 205° C. From 60° C., a mixture of 5.5 g (0.075 mol) of diethylamine and 3 ml of 1,2,4-trichlorobenzene was added to the reaction solution in the course of 5.5 hours. The solvent was evaporated and the crystallizing residue was boiled in water, and the mixture was cooled, filtered and dried. 4.2 g of N-(4-ethoxyphenyl)-N',N'-diethylurea, i.e. 76% of theory, having a melting point of 95° to 98° C. were obtained in this way.

EXAMPLE 12

N-(4-chlorophenyl)-N'-methylurea 2.82 g (0.038 mol) of N-methylurea and 3.19 g of 95% pure 4-chloroaniline (0.025 mol) were added into 28 ml of 1,2,4-trichlorobenzene. The mixture was slowly heated to 205° C. with stirring, methylamine being passed into the mixture from 60° C. After 5.5 hours, 15.2 g (0.35 mol) of methylamine had been introduced and the reaction was complete. The solvent was evaporated and the crude product obtained was purified by means of a silica gel column (Merck 9385, eluent tetrahydrofuran: cyclohexane 2:1).

3.2 g of N-(4-chlorophenyl)-N'-methylurea, i.e. 69% of theory, having a melting point of 204° to 206° C. were obtained in this way. After recrystallizing from ethanol:water=7:3, a melting point of 206° to 208° C. was obtained.

EXAMPLE 13

N-(4-chlorophenyl)-N'-butyl-N'-methylurea 3.19 g (0.025 mol) of pract. 4-chloroaniline were mixed with 4.95 g (0.038 mol) of N-butyl-N-methylurea in 25 ml of 1,2,4-trichlorobenzene and the mixture was slowly heated to 205° C. with stirring. From 100° C., a solution of 6.6 g (0.075 mol) of N-butyl-N-methylamine in 3 ml of 1,2,4-trichlorobenzene was introduced into the reaction mixture in the course of 4 hours. The reaction mixture was kept at this temperature for 4 hours and then cooled to 20° C., whereupon a precipitate deposited. The precipitate deposited was filtered off, washed with 1,2,4-trichlorobenzene and petroleum ether and dried in vacuo at 80° C. The crude product obtained was boiled with 60 ml of water, cooled to 20° C., and the precipitate was filtered off with suction, washed with water and dried at 70° C. in vacuo.

2.9 g of N-(4-chlorophenyl)-N'-butyl-N'-methylurea, i.e. 48% of theory, having a melting point of 115° to 117° C. were obtained in this way.

N-butyl-N-methylurea 18 g (0.3 mol) of urea were suspended in 50 ml of xylene. The suspension was heated to 130° to 135° C. and a solution of 26.15 g (0.3 mol) of N-butyl-N-methylamine in 25 ml of xylene was added with stirring. At this point, the mixture was evaporated to half its volume and cooled, whereupon a precipitate deposited. The precipitate was filtered off, washed with a little xylene and dried in vacuo at 70° C.

27.3 g of N-butyl-N-methylurea, i.e. 70% of theory, having a melting point of 84° to 88° C. were obtained in this way.

EXAMPLE 14

N-(4-(4-chlorophenoxy)phenyl)-N'-N'-dimethylurea 3.35 g (0.038 mol) of N,N-dimethylurea and 5.49 g (0.025 mol) of 4-amino-4'-chloro diphenyl ether were added into 28 ml of 1,2,4-trichlorobenzene with stirring. The reaction mixture was heated to 205° C., dimethylamine being introduced from 60° C. After 5.5 hours, 15.1 g (0.33 mol) of dimethylamine had been passed in and the reaction was complete. The reaction mixture was cooled to room temperature, whereupon a precipitate deposited. The precipitate was filtered off, washed with 1,2,4-trichlorobenzene, dried and then boiled in water. The aqueous mixture was cooled, and the precipitate was filtered off with suction and dried. 5.75 g of N-(4-(4-chlorophenoxy)phenyl)-N',N'-dimethylurea, which corresponds to 79% of theory, having a melting point of 150° to 152° C. were obtained in this way.

The melting points were determined using a Kofler micromelting point apparatus.

The purity of the products prepared according to Examples 1 to 6 was determined by HPLC analysis.

What we claim is:

1. Process for the preparation of pure, unsymmetrically disubstituted ureas of the formula

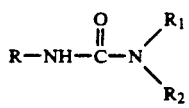

I in which R denotes a phenyl radical which is unsubstituted, or monosubstituted or polysubstituted by halogen atoms or alkyl, alkoxy, aryloxy or trifluoromethyl groups, an oxazolyl, isoxazolyl, thiazolyl, isothiazolyl, benzoxazolyl or benzothiazolyl radical which is unsubstituted, or monosubstituted or polysubstituted by halogen atoms or alkyl, alkoxy or trifluoromethyl groups and $R_1$ and $R_2$ independently of one another denote a hydrogen atom or an alkyl group, where $R_1$ and $R_2$ are not simultaneously hydrogen or $R_1$ and $R_2$ together denote a butylene or pentylene group, comprising reacting an N-alkyl- or N,N-dialkylurea of the formula

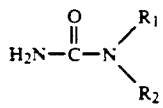

in which $R_1$ and $R_2$ have the abovementioned meaning, in a diluent or not, with an amine of the formula

in which R has the abovementioned meaning, in the presence of an excess of an amine of the formula

in which $R_1$ and $R_2$ in each case have the same meaning as in the N-alkyl- or N,N-dialkylurea employed of the formula II and isolating the reaction product of the formula I.

2. Process according to claim 1, comprising preparing the N-alkyl- or N,N-dialkylurea of the formula II by reaction of urea with an amine of the formula IV, in a diluent or not, and reacting without isolation giving the unsymmetrically disubstituted urea of the formula I.

3. Process according to claim 1, comprising carrying out the reaction in a diluent.

4. Process according to claim 3, comprising carrying out the reaction in trichlorobenzene.

5. Process according to claim 1, comprising employing the mother liquor which is obtained after the isolation of the reaction product of the formula I according to claim 1 as the diluent in a further reaction for the preparation of the same reaction product of the formula I.

6. Process according to claim 1, comprising employing an N-alkyl- or N,N-dialkylurea of the formula II and an amine of the formula IV in which $R_1$ and $R_2$ in each case independently of one another denote alkyl groups having 1 to 4 C atoms, $R_1$ and $R_2$ in formula II and in formula IV having the same meaning.

7. Process according to claim 6, comprising employing dimethylurea as the N-alkyl- or N,N-dialkylurea and dimethylamine as the amine of the formula IV.

8. Process according to claim 1, comprising employing an amine of the formula III in which R denotes a phenyl radical which is unsubstituted, or monosubstituted or polysubstituted by halogen atoms, or alkyl or alkoxy groups.

9. Process according to claim 1, comprising employing 2 to 15 mol of the amine of the formula IV per mol of the N-alkyl- or N,N-dialkylurea of the formula II.

10. Process according to claim 1, comprising employing 0.5 to 0.7 mol of the amine of the formula III per mol of the N-alkyl- or N,N-dialkylurea of the formula II.

* * * * *